(12) United States Patent
Meyer et al.

(10) Patent No.: US 8,090,183 B2
(45) Date of Patent: Jan. 3, 2012

(54) PATTERN NOISE CORRECTION FOR PSEUDO PROJECTIONS

(75) Inventors: Michael G. Meyer, Seattle, WA (US); Jon W. Hayenga, Redmond, WA (US); Thomas M. Abbott, Issaquah, WA (US); David E. Steinhauer, Lynnwood, WA (US)

(73) Assignee: Visiongate, Inc., Phoenix, AZ (US)

( * ) Notice: Subject to any disclaimer, the term of this patent is extended or adjusted under 35 U.S.C. 154(b) by 519 days.

(21) Appl. No.: 12/403,231

(22) Filed: Mar. 12, 2009

(65) Prior Publication Data
US 2010/0232664 A1    Sep. 16, 2010

(51) Int. Cl.
G06K 9/18  (2006.01)

(52) U.S. Cl. ............. 382/133; 382/172; 382/260; 378/4

(58) Field of Classification Search ............... 382/133, 382/131, 172, 260, 134; 356/326, 73, 419; 378/4, 8, 901
See application file for complete search history.

(56) References Cited

U.S. PATENT DOCUMENTS

| | | |
|---|---|---|
| 3,657,537 A | 4/1972 | Wheeless, Jr. |
| 3,705,771 A | 12/1972 | Friedman et al. |
| 3,748,468 A | 7/1973 | Hartman |
| 3,960,449 A | 6/1976 | Carlton |
| 3,999,047 A | 12/1976 | Green |
| 4,110,043 A | 8/1978 | Eisert |
| 4,175,860 A | 11/1979 | Bacus |
| 4,183,623 A | 1/1980 | Haines |
| 4,293,221 A | 10/1981 | Kay |
| 4,360,885 A | 11/1982 | Edgar |
| 4,667,830 A | 5/1987 | Nozaki, Jr. et al. |
| 4,694,342 A | 9/1987 | Klees |
| 4,702,598 A | 10/1987 | Bohmer |
| 4,747,156 A | 5/1988 | Wahl |
| 4,786,165 A | 11/1988 | Yamamoto |
| 4,858,128 A | 8/1989 | Nowak et al. |

(Continued)

FOREIGN PATENT DOCUMENTS
WO    2006016290 A1    2/2006

OTHER PUBLICATIONS

Bogdan, M. and Fita, S., "Elimination of the CCD Camera Noise in Microscopic Measurements of Machine Elements," Measurement Science Review, 2003, vol. 3 section 3.

(Continued)

*Primary Examiner* — Francis M Legasse, Jr.
(74) *Attorney, Agent, or Firm* — George A. Leone; Citadel Patent Law

(57) ABSTRACT

Correcting pattern noise projection images includes acquiring a set of projection images with an optical tomography system including a processor, where each of the set of projection images is acquired at a different angle of view. A threshold is applied to each projection image produce a set of threshold images. Each threshold image may optionally be dilated to produce a set of dilated images that are summed to form an ensemble image. Each of the dilated images is processed to produce a set of binary images. The set of binary images are summed to form an ensemble mask. The ensemble image is divided by the ensemble mask to yield a background pattern noise image. Each projection image is multiplied by a scaling factor and divided by the background pattern noise to produce a quotient image that is filtered to produce a noise corrected projection image.

22 Claims, 13 Drawing Sheets

U.S. PATENT DOCUMENTS

| | | | |
|---|---|---|---|
| 4,873,653 | A | 10/1989 | Grosskopf |
| 5,034,613 | A | 7/1991 | Denk |
| 5,117,466 | A | 5/1992 | Buican |
| 5,141,609 | A | 8/1992 | Sweedler |
| 5,148,502 | A | 9/1992 | Tsujiuchi |
| 5,159,398 | A | 10/1992 | Maekawa et al. |
| 5,189,518 | A | 2/1993 | Nishida et al. |
| 5,333,164 | A | 7/1994 | Tam |
| 5,390,226 | A | 2/1995 | Tam |
| 5,402,460 | A | 3/1995 | Johnson |
| 5,539,800 | A | 7/1996 | Katsevich |
| 5,548,395 | A | 8/1996 | Kosaka |
| 5,550,892 | A | 8/1996 | Katsevich |
| 5,644,388 | A | 7/1997 | Maekawa et al. |
| 5,680,484 | A | 10/1997 | Ohyama |
| 5,689,590 | A | 11/1997 | Shirasawa et al. |
| 5,710,429 | A | 1/1998 | Alfano |
| 5,757,981 | A | 5/1998 | Kawakubo |
| 5,760,901 | A | 6/1998 | Hill |
| 5,760,951 | A | 6/1998 | Dixon |
| 5,768,440 | A | 6/1998 | Campanelli et al. |
| 5,771,070 | A | 6/1998 | Ohzu et al. |
| 5,831,723 | A | 11/1998 | Kubota |
| 5,848,181 | A | 12/1998 | Ogata |
| 5,878,103 | A | 3/1999 | Sauer |
| 5,880,838 | A | 3/1999 | Marx et al. |
| 5,909,476 | A | 6/1999 | Cheng et al. |
| 5,915,048 | A | 6/1999 | Hill et al. |
| 5,926,224 | A | 7/1999 | Nagasawa |
| 5,987,158 | A | 11/1999 | Meyer |
| 6,026,174 | A | 2/2000 | Palcic |
| 6,028,957 | A | 2/2000 | Katori et al. |
| 6,038,067 | A | 3/2000 | George |
| 6,072,624 | A | 6/2000 | Dixon et al. |
| 6,078,681 | A | 6/2000 | Silver |
| 6,091,983 | A | 7/2000 | Alfano et al. |
| 6,130,958 | A | 10/2000 | Rohler et al. |
| 6,165,734 | A | 12/2000 | Garini |
| 6,177,277 | B1 | 1/2001 | Soini |
| 6,201,628 | B1 | 3/2001 | Basiji |
| 6,211,955 | B1 | 4/2001 | Basiji |
| 6,215,587 | B1 | 4/2001 | Alfano et al. |
| 6,248,988 | B1 | 6/2001 | Krantz |
| 6,249,341 | B1 | 6/2001 | Basiji et al. |
| 6,251,586 | B1 | 6/2001 | Mulshine |
| 6,251,615 | B1 | 6/2001 | Oberhardt |
| 6,252,979 | B1 | 6/2001 | Lee |
| 6,256,096 | B1 | 7/2001 | Johnson |
| 6,295,384 | B1 | 9/2001 | Into |
| 6,433,822 | B1 | 8/2002 | Clark et al. |
| 6,463,182 | B1 | 10/2002 | Onishi et al. |
| 6,473,176 | B2 | 10/2002 | Basiji |
| 6,519,355 | B2 | 2/2003 | Nelson |
| 6,522,775 | B2 | 2/2003 | Nelson et al. |
| 6,532,310 | B1 | 3/2003 | Into |
| 6,591,003 | B2 | 7/2003 | Chu et al. |
| 6,608,682 | B2 | 8/2003 | Ortyn et al. |
| 6,621,937 | B1 | 9/2003 | Adams, Jr. et al. |
| 6,636,623 | B2 | 10/2003 | Nelson et al. |
| 6,640,014 | B1 | 10/2003 | Price |
| 6,646,246 | B1 | 11/2003 | Gindele et al. |
| 6,667,766 | B2 | 12/2003 | Matsutani et al. |
| 6,697,508 | B2 | 2/2004 | Nelson |
| 6,741,730 | B2 | 5/2004 | Rahn et al. |
| 6,741,752 | B1 | 5/2004 | Yang |
| 6,763,142 | B2 | 7/2004 | Dai et al. |
| 6,770,893 | B2 | 8/2004 | Nelson |
| 6,775,399 | B1 | 8/2004 | Jiang |
| 6,801,672 | B1 | 10/2004 | Thomas |
| 6,850,587 | B1 | 2/2005 | Karimi |
| 6,931,160 | B2 | 8/2005 | Gindele et al. |
| 6,937,772 | B2 | 8/2005 | Gindele |
| 6,944,322 | B2 | 9/2005 | Johnson et al. |
| 6,975,400 | B2 | 12/2005 | Ortyn et al. |
| 7,003,143 | B1 | 2/2006 | Hewitt |
| 7,039,455 | B1 | 5/2006 | Brosovich et al. |
| 7,050,650 | B2 | 5/2006 | Maurer et al. |
| 7,092,017 | B2 | 8/2006 | Kelly et al. |
| 7,113,647 | B2 | 9/2006 | Nara |
| 7,136,100 | B1 | 11/2006 | Kato et al. |
| 7,141,773 | B2 | 11/2006 | Kaplan et al. |
| 7,173,261 | B2 | 2/2007 | Ogawa et al. |
| 7,197,355 | B2 | 3/2007 | Nelson |
| 7,218,393 | B2 | 5/2007 | Sharpe et al. |
| 7,224,540 | B2 | 5/2007 | Olmstead et al. |
| 7,253,627 | B1 | 8/2007 | Ahmed |
| 7,260,253 | B2 | 8/2007 | Rahn et al. |
| 7,274,809 | B2 | 9/2007 | MacAulay et al. |
| 7,280,135 | B2 | 10/2007 | Kim |
| 7,362,911 | B1 * | 4/2008 | Frank ............................ 382/260 |
| 7,391,447 | B2 | 6/2008 | Lee et al. |
| 7,433,537 | B2 | 10/2008 | Sasada |
| 7,443,431 | B2 | 10/2008 | Kelly et al. |
| 7,479,993 | B2 | 1/2009 | Nakajima et al. |
| 7,505,549 | B2 * | 3/2009 | Ohishi et al. ...................... 378/4 |
| 7,508,982 | B2 | 3/2009 | Tsuyuki et al. |
| 7,518,647 | B2 | 4/2009 | Kim et al. |
| 2002/0045812 | A1 | 4/2002 | Ichihashi |
| 2002/0106051 | A1 * | 8/2002 | Menhardt ........................ 378/4 |
| 2002/0122167 | A1 | 9/2002 | Riley et al. |
| 2003/0199758 | A1 | 10/2003 | Nelson |
| 2004/0001618 | A1 | 1/2004 | Johnson |
| 2004/0076319 | A1 | 4/2004 | Fauver et al. |
| 2004/0197839 | A1 | 10/2004 | Daniely et al. |
| 2004/0217256 | A1 | 11/2004 | Ortyn et al. |
| 2004/0228520 | A1 | 11/2004 | Dresser |
| 2005/0006595 | A1 | 1/2005 | Goodwin et al. |
| 2005/0010108 | A1 | 1/2005 | Rahn et al. |
| 2005/0085708 | A1 | 4/2005 | Fauver et al. |
| 2005/0085721 | A1 | 4/2005 | Fauver et al. |
| 2005/0270425 | A1 | 12/2005 | Min |
| 2006/0023219 | A1 | 2/2006 | Meyer et al. |
| 2006/0066837 | A1 | 3/2006 | Ortyn et al. |
| 2006/0068371 | A1 | 3/2006 | Ortyn et al. |
| 2006/0093200 | A1 | 5/2006 | Sharpe et al. |
| 2006/0096358 | A1 | 5/2006 | Fauver et al. |
| 2006/0099707 | A1 | 5/2006 | Nelson et al. |
| 2006/0183220 | A1 | 8/2006 | Nelson et al. |
| 2006/0204071 | A1 | 9/2006 | Ortyn et al. |
| 2007/0071357 | A1 | 3/2007 | Rahn et al. |
| 2007/0146873 | A1 | 6/2007 | Ortyn et al. |
| 2007/0211928 | A1 | 9/2007 | Weng et al. |
| 2007/0215528 | A1 | 9/2007 | Hayenga et al. |
| 2007/0258122 | A1 | 11/2007 | Champoulov et al. |
| 2008/0151081 | A1 | 6/2008 | Frank |
| 2008/0194946 | A1 | 8/2008 | Summers et al. |
| 2008/0239110 | A1 | 10/2008 | Hara |

OTHER PUBLICATIONS

Schmitz, et al., "Performance Characteristics of a Silicon Photodiode (SiPD) Based Instrument for Fast Functional Optical Tomography," SUNY Downstate Medical Center, 2001, Brooklyn, NY 11203.

Schmitz, et al., "Instrument for Real-Time Dynamic Optical Tomography," SUNY Downstate Medical Center, 2002, Brooklyn, NY 11203.

King, M.C. and D. H. Berry, D.H., A Depth Scanning Microscope, Applied Optics, vol. 10, No. 1, Jan. 1971, pp. 208-210.

Bellman, S.H. et al., "ART is Science being a Defense of Algebraic Reconstruction Techniques for Three dimensional Electron Microscopy," Journal of Theoretical Biology, 1971, 32 pp. 205-216.

Gilbert, P., "Iterative Methods for the Three dimensional Reconstruction of an Object from Projections," Journal of Theoretical Biology, 1972, 36 pp. 105-117.

Oppenheim, B. E., "More Accurate Algorithms for Iterative 3 dimensional Reconstruction," IEEE Transactions on Nuclear Science, 1974, NS-21 pp. 72-77.

Shannon, The Art and Science of Optical Design, (1977) University of Arizona, Cambridge University Press, Fig. 4.12 and Fig. 4.13.

Klug, A, "Image analysis and reconstruction in the electron microscopy of biological macromolecules," Chem. Scripta, 1979, vol. 14, p. 245.

Anderson, R. H., "Close-up imaging of documents and displays with lens arrays," AppliedOptics 1979, 18, 477.

Herman, G, "Image Reconstruction from Projections: The Fundamentals of Computerized Tomography," Academic Press, 1980, New York.

Pieper, R.J. and Korpel A., Image processing for extended depth of field, Applied Optics, May 15, 1983, vol. 22, No. 10, pp. 1449-1453.

Reymond et al., "A Routine Flat Embedding Method for Electron Microscopy of Microorganisms Allowing Selection and Precisely Orientated Sectioning of Single Cells by Light Microscopy," Journal of Microscopy, Apr. 1983, vol. 130 Pt. 1 pp. 79-84.

Ong, S. H., "Development of an imaging flow cytometer." Anal Quant Cytol Histol, 1987, 9(5)pp. 375-382.

Kak, A.C. and Slaney, M., "Principles of Computerized Tomographic Imaging," IEEE Press, 1988, New York.

Singer, J. R. et al., "Image Reconstruction of the Interior of Bodies that Diffuse Radiation," Science 248(4958),1990, pp. 990-993.

Kikuchi, S., "Three-dimensional computed tomography for optical microscopes," Optics Communications, 1994, 107, pp. 432-444.

Tiziani, H. J. et al., "Three-dimensional analysis by a microlens array confocal arrangements" Applied Optics, (1994) 33, 567.

Paulsen, K. D., "Spatially Varying Optical Property Reconstruction Using a Finite Element Diffusion Equation Approximation," Medical Physics, 1995, vol. 22 pp. 691-701.

Shapiro, H. M., Practical Flow Cytometry, 3rd ed., 1995, Wiley-Liss.

Defrise, M., "Image Reconstruction from Truncated, Two-dimensional, Parallel Projections," Inverse Problems, 1995, 11 pp. 287-313.

Pawley, J. B., "Handbook of Biological Confocal Microscopy," 1995, Plenum Press, NY 479-490.

Wedberg, T.C., "Recent results in optical diffraction microtomography," Meas. Sci. Technol., 1996, vol. 7, p. 414.

Kikuchi, S. et al., "Three-dimensional microscope computed tomography based on general Radon transform for optical imaging systems," Optics Communications 123 (1996) 725-733.

Sheppard, C. J. R. & Torok, P., "Effects of specimen refractive index on confocal imaging," Journal of Microscopy, Mar. 1997, vol. 185, Pt. 3, pp. 366-374.

Taguchi, K. and Aradate, H., "Algorithm for Image Reconstruction in Multi-slice Helical CT", Medical Physics, 1998, 25(4) pp. 550-561.

Hampel, U and Freyer, R, "Fast Image Reconstruction for Optical Absorption Tomography in Media with Radially Symmetric Boundaries," Medical Physics, 1998, 25 (1)pp. 92-101.

Tucker, S.C. et al., "Extended depth of field and aberration control for inexpensive digital microscope systems," Optics Express, May 24, 1999, vol. 4, No. 11, pp. 467-474.

Edelmann, P. et al., "Correlation of chromatic shifts and focal depth in Spectral Precision Distance Microscopy measured by Micro Axial Tomography," Optical Biopsies and Microscopic Techniques III, Sep. 1999, SPIE vol. 3568, pp. 89-95.

George, JS et al., "Virtual Pinhole Confocal Microscope," Physics Division Progress Report, 1999, www.lanl.gov/p/pdfs/papp_pinhole.pdf.

Defrise, M. et al., "A Solution to the Long-object Problem in Helical Cone-beam Tomography," Physics in Medicine and Biology, 2000, 45(623-43).

Yu, D. F. et al., Maximum-Likelihood Transmission Image Reconstruction for Overlapping Transmission Beams, IEEE Transactions on Medical Imaging, 2000, 19(11)pp. 1094-1105.

Sanyal, S. and Ghosh, A., High focal depth with a quasi-bifocus birefringent lens, Applied Optics,May 10, 2000, vol. 39, No. 14, pp. 2321-2325.

Herzenberg, L. A., The History and Future of the Fluoresence Activated Cell Sorter and Flow Cytometry: A View from Stanford, 2002.

Sharpe, J. et al., "Optical Projection Tomography as a Tool for 3D Microscopy and Gene Expression Studies," Science, Apr. 19, 2002, vol. 296, pp. 541-545.

Widjanarko, T., et al., "A post-processing technique for extending depth of focus in conventional optical microscopy," Optics & Laser Technology, 2002, 34 pp. 299-305.

Martini, N. et al., A new high-aperture glycerol immersion objective lens and its application to 3D-fluoresence microscopy, Journal of Microscopy, May 2002, vol. 206 Pt. 2, pp. 146-151.

Matula, P. et al., "Precise 3D image alignment in micro-axial tomography," Journal of Microscopy, Feb. 2003, vol. 209, Pt. 2 pp. 126-142.

Sharpe, J. et al., Review, "Optical Projection Tomography as a New Tool for Studying Embryo Anatomy," J. Anat. 2003, pp. 175-181.

Lane, P.M. et al., "Confocal Microendoscopy with Chromatic Sectioning," Spectral Imaging: Instrumentation, Applications, and Analysis II, Proc. of SPIE, 2003, vol. 4959 pp. 23-26.

Fauver et al., "Development of Micro-Optical Projection Tomography for 3D Analysis of Single Cells, Image Acquisition and Processing XI," Edited by Conchello, Jose-Angel; Cogswell, Carol J.; Wilson, Tony. Proceedings of the SPIE, 2004, vol. 5324, pp. 171-181.

Fauver et al., "Three-dimensional imaging of single isolated cell nuclei using optical projection tomography," Optics Exress, May 30, 2005, vol. 13 No. 11/4210-4223.

Abragamsson, S. et al., "A new approach to extended focus for high-speed, high-resolution biological microscopy," Proc. of SPIE, 2006, vol. 60900, N1-N8.

Mikula, G. et al., "Imaging with extended focal depth by means of lenses with radial and angular modulation," Optics Express, Jul. 23, 2007, vol. 15, No. 15, pp. 9184-9193.

Kerfoot, et al., "Quantitative Multiplex Chromagenic Immunohistochemistry," Mosaic Laboratories, 2007, www.mosaiclabs.com, Tuscon Symposium.

Xu, Y. et al., "Ultra long high resolution beam by multi-zone rotationally symmetrical complex pupil filter," Optics Express, May 10, 2007, vol. 15, No. 10, pp. 6409-6413.

Conchello, J-A. et al., "Extended depth-of-focus microscopy via constrained deconvolution," Journal of Biomedical Optics 12 (6), 064026 (Nov./Dec. 2007).

Smolinska and Dawidowicz, "Extraction of common or different part from optical images," Institute of Physics, Warsaw Technical University, 222-223.

Meyer, et al., "Automated cell analysis in 2D and 3D: A comparative study," Science Direct: Pattern Recognition, 2009, 42 pp. 141-146.

* cited by examiner

PATTERN NOISE CORRECTION FOR PSEUDO PROJECTIONS

FIELD OF THE INVENTION

The present invention relates generally to analysis of medical imaging data, and, more particularly, to pattern noise correction in a biological cell imager.

BACKGROUND OF THE INVENTION 3D tomographic reconstructions require projection images as input. A projection image assumes that an object of interest is translucent to a source of exposure such as a light source transmitted through the object of interest. The projection image, then, comprises an integration of the absorption by the object along a ray from the source to the plane of projection. Light in the visible spectrum is used as a source of exposure in optical projection tomography.

In the case of producing projections from biological cells, the cells are typically stained with hematoxyln, an absorptive stain that attaches to proteins found cell chromosomes. Cell nuclei are approximately 15 microns in diameter, and in order to promote reconstructions of sub-cellular features it is necessary to maintain sub-micron resolution. For sub-micron resolution, the wavelength of the illuminating source is in the same spatial range as the biological objects of interest. This can result in undesirable refraction effects. As a result a standard projection image cannot be formed. To avoid these undesirable effects, as noted above, the camera aperture is kept open while the plane of focus is swept through the cell. This approach to imaging results in equal sampling of the entire cellular volume, resulting in a pseudo-projection image. A good example of an optical tomography system has been published as United States Patent Application Publication 2004-0076319, on Apr. 22, 2004, corresponding to pending U.S. patent application Ser. No. 10/716,744, filed Nov. 18, 2003, to Fauver, et al. and entitled "Method and Apparatus of Shadowgram Formation for Optical Tomography." U.S. patent application Ser. No. 10/716,744 is incorporated herein by reference.

Pattern Noise

Pattern noise represents a kind of distortion that is fixed and present to the same degree for all pseudo-projection images acquired in any optical tomography system. The source of this distortion is any component in the optical path from illumination to the image formation that causes light to deviate from its ideal path in a way that is consistent from projection to projection. Pattern noise does not arise from the cell or any components in the cell-CT that are in movement during collection of the pseudo-projection images.

Referring, for example, to FIG. 2, a typical pseudo-projection image exhibiting some causes of pattern noise is shown. These include dust and illumination variation. Also shown in FIG. 2 are two cells C1, C2 embedded in an optical gel. In a system employing a CCD camera for acquiring pseudo projections or the like sources of pattern noise include:

1. Non-constant illumination,
2. Dust on a CCD camera,
3. Non-uniformity in the CCD camera response, and
4. Distortions in illumination arising from dirt/debris on the reflecting surfaces encountered in the optical path.

Referring now to FIG. 2A, there shown is a selected portion 40 of the pseudo-projection image that has been enhanced as section 40A to better visually illustrate some subtle effects of pattern noise. Section 40A exhibits more subtle distortion that results from dirt and debris on the reflecting surfaces in the optical path. This distortion is exemplified by taking a segment of the pseudo projection and expanding it to fill the entire space gray scale dynamic range. Note the mottling distortion in the background 44.

Distortions Arising from Pattern Noise

Using an optical tomography system as described in Fauver, pseudo-projection images are formed as an object, such as a cell, is rotated. The formed pseudo-projection images are back-projected and intersected to form a 3D image of the cell. The pattern noise in the pseudo projections is also intersected and results in a noise that is additive to the reconstruction of the object of interest. While noise in each pseudo projection may be rather small, in the resulting reconstruction this noise may be quite large as the patterning may reinforce in a constructive way across multiple pseudo projections.

Referring now to FIG. 3, a reconstructed slide that has been enhanced to show the effect of the pattern noise on a reconstructed image is shown. The swirling pattern 30 in the background is one obvious manifestation of pattern noise.

Unfortunately, previously known techniques for spatial filtering do not adequately correct images because they do not effectively address the causes of pattern noise. Spatial filtering does not adequately correct for low frequency illumination variations. Further, spatial filtering does not adequately remove impulse distortions, arising from dust. Further still, the spatial frequency of pattern noise in the form of mottling is in the same range as other features whose 3D reconstruction is desired. Consequently a different approach to pattern noise removal is needed.

The present invention described herein provides, for the first time, a new and novel system and method for removing the detrimental effects of pattern noise in medical imagers.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A system and method for correcting pattern noise projection images includes acquiring a set of projection images with an optical tomography system including a processor, where each of the set of projection images is acquired at a different angle of view. A threshold is applied to each projection image produce a set of threshold images. Each threshold image may optionally be dilated to produce a set of dilated images. The set of threshold images (or dilated images) are summed to form an ensemble image. Each of the threshold images (or dilated images) is processed to produce a set of binary images. The set of binary images are summed to form an ensemble mask. The ensemble image is divided by the ensemble mask to yield a background pattern noise image. Each projection image is multiplied by a scaling factor and divided by the background pattern noise to produce a quotient image that is filtered to produce a noise corrected projection image.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DESCRIPTION OF THE PREFERRED EMBODIMENT

Figure 1:
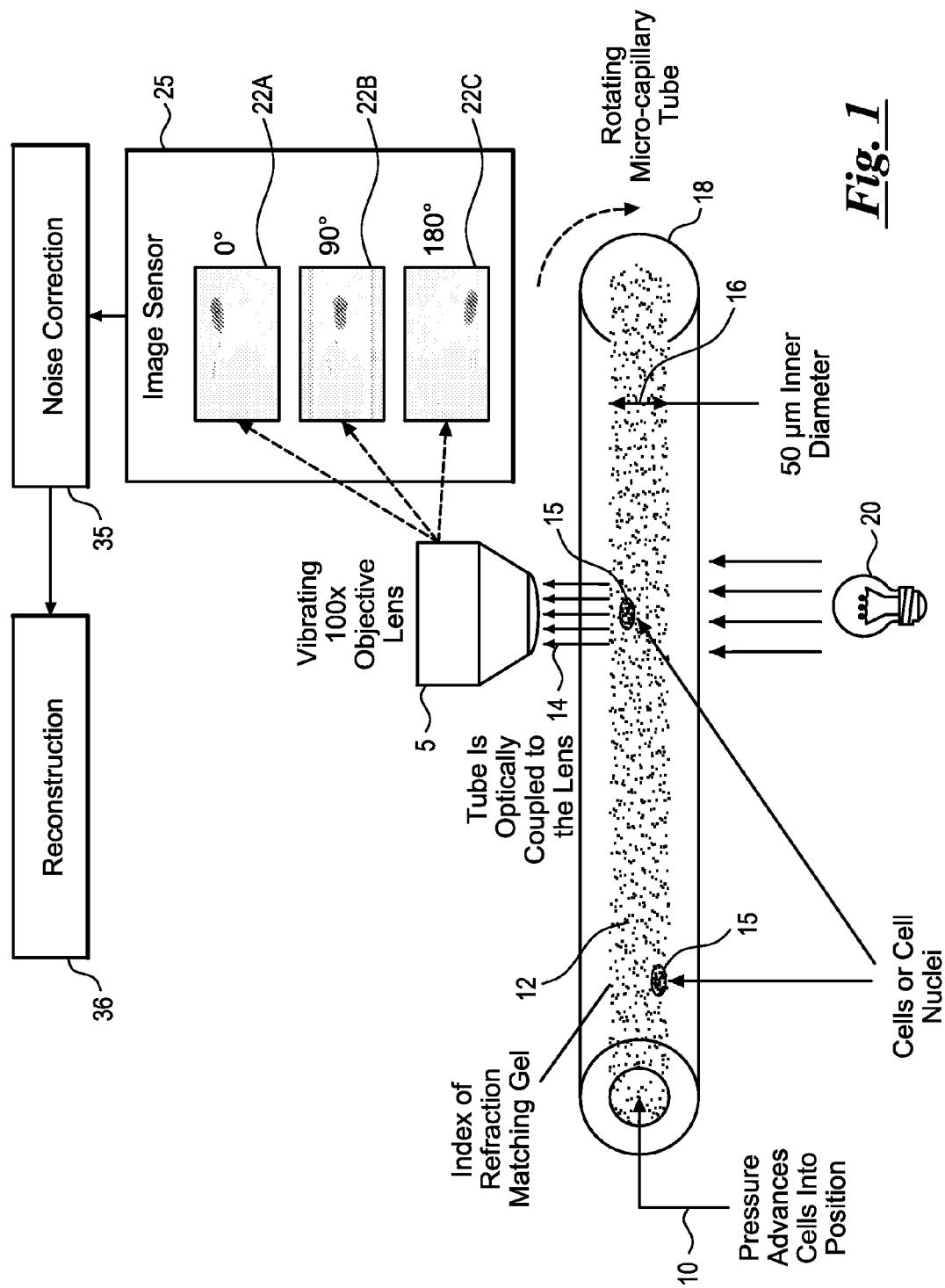
FIG. 1 is a highly schematic view of an optical projection tomography system including a pattern noise correction processor.

The following disclosure describes several embodiments and systems for imaging an object of interest. Several features of methods and systems in accordance with example embodiments of the invention are set forth and described in the figures. It will be appreciated that methods and systems in accordance with other example embodiments of the invention can include additional procedures or features different than those shown in figures.

Example embodiments are described herein with respect to biological cells. However, it will be understood that these examples are for the purpose of illustrating the principles of the invention, and that the invention is not so limited. Additionally, methods and systems in accordance with several example embodiments of the invention may not include all of the features shown in these figures. Throughout the figures, like reference numbers refer to similar or identical components or procedures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or various combinations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Generally as used herein the following terms have the following meanings when used within the context of optical microscopy processes:

"Capillary tube" has its generally accepted meaning and is intended to include transparent microcapillary tubes and equivalent items with an inside diameter generally of 500 microns or less.

"Depth of field" is the length along the optical axis within which the focal plane may be shifted before an unacceptable image blur for a specified feature is produced.

"Object" means an individual cell, item, thing, particle or other microscopic entity.

"Pseudo projection" includes a single image representing a sampled volume of extent larger than the native depth of field of a given set of optics. One concept of a pseudoprojection is taught in Fauver '744.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Sample" means a finished cellular preparation that is ready for analysis, including all or part of an aliquot or specimen.

As used in this specification, the terms "processor" and "computer processor" encompass a personal computer, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent including related memory devices, transmission devices, pointing devices, input/output devices, displays and equivalents.

Referring now to FIG. 1 a highly schematic view of an optical projection tomography system including a pattern noise correction processor is shown. Cells 15 are suspended in an index of refraction matching gel 12 contained in a capillary tube 18. Pressure 10 is applied to the gel 12 to move the cells into the optical path of a high-magnification microscope including an objective lens 5. The objective lens 5 is scanned or vibrated by, for example, a (not shown) piezoelectric element. The capillary tube 18 is positioned to be scanned by the vibrating objective lens 5. An illumination source 20 operates to illuminate objects, such as biological cells passing through the field of view of the objective lens 5. An image sensor 25 is located to acquire images transmitted from the objective lens 5. A plurality of pseudo-projection images, here exemplified by pseudo-projection images 22A, 22B and 22C are acquired by the image sensor 25 at varying angles of view as presented by the rotating capillary tube 18. An image processor with noise correction 35 is coupled to receive the pseudo-projection images. Corrected pseudo-projection images are then passed to a reconstruction processor 36 for producing 3-D images.

VisionGate, Inc. of Gig Harbor Washington, assignee of this application, is developing an optical tomography system incorporating pattern noise correction under the trademark "Cell-CT™."The Cell-CT™optical tomography system employs scores, designed to detect lung cancer in its preinvasive and treatable stage. In one example embodiment the operation is as follows.

Figure 3:
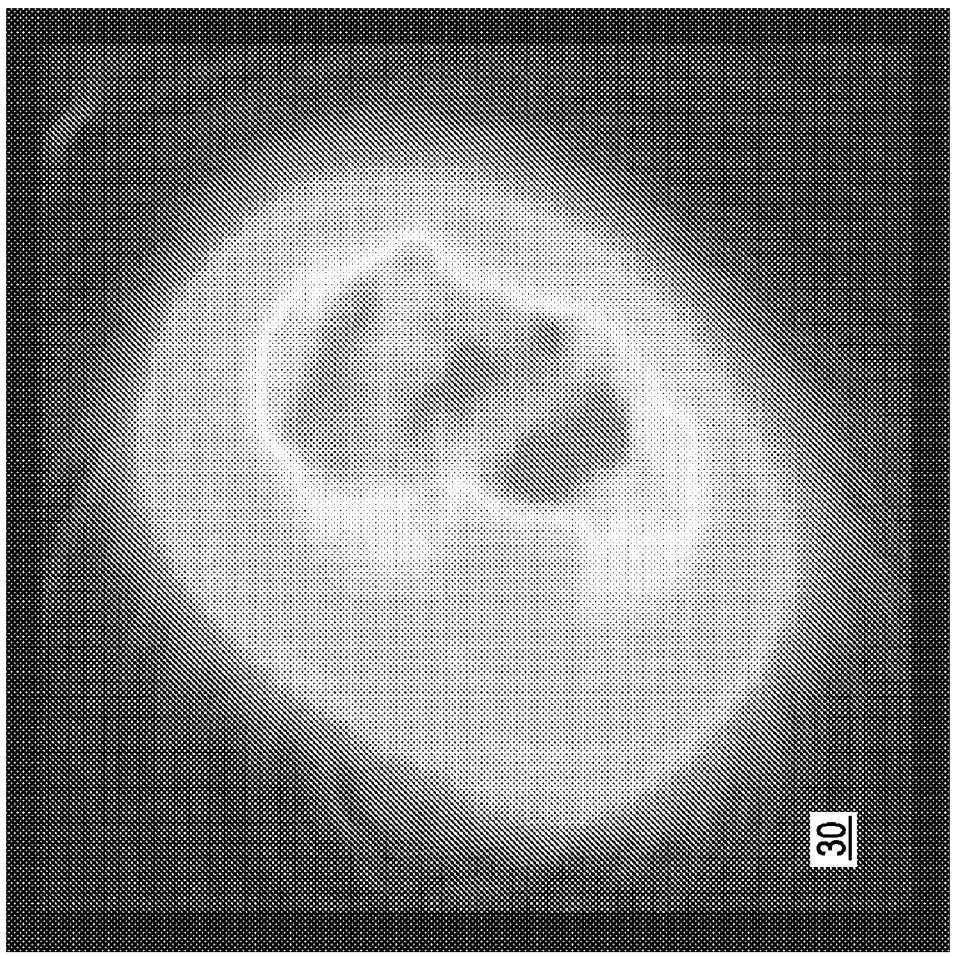
FIG. 3 shows a processed slice from 3D reconstruction showing the effect of pattern noise.

1. A specimen for examination is processed to remove non-diagnostic elements and is fixed and stained.
2. The specimen is then suspended in a gel medium. The cells in gel mixture are then inserted into a glass microcapillary tube 18 of approximately 50μ inner diameter 16.
3. Pressure is applied to the gel to move the cells into the optical path 14 of a high-magnification microscope.
4. Once the cells are in place the tube is rotated to permit capture of 500 high resolution images of the desired object taken over 360 degrees of tube rotation. These images are simulations of projection images created by integrating the light from the objective lens as the objective scans the nucleus. The simulated projection or pseudo-projection images thus represent the entire nuclear content in a single image, taken from a single perspective.
5. Pseudo-projection images are processed to correct for residual noise and motion artifact.
6. The corrected pseudo projections are processed using filtered back projection to yield a 3-D tomographic representation of the cell. An example section of such a 3-D rendering is shown in FIG. 3 for an Adenocarcinoma cell grown in culture.
7. Based on the tomographic reconstruction, features are computed that are used to detect cells with the characteristics of cancer and its precursors. These features are used in a classifier whose output designates the likelihood that object under investigation is a cancer cell. Classifier outputs are based on a scoring system developed by VisionGate, Inc. called LuCED™ scores.

Among other things, good quality reconstruction and classification depends on good quality corrected pseudo projections input to the reconstruction algorithm in step 6. This document discloses a method to correct for pattern noise present in pseudo projections at the time of data capture.

Pattern Noise Correction

As noted above, pattern noise results from additive distortion. A pseudo projection may be modeled as an ideal pseudo projection plus pattern noise. If the pattern noise is found then the ideal, noise free, pseudo projection can be found by subtracting the pattern noise from the noisy pseudo projection. Hence a challenge for doing a subtractive correction is to find the pattern noise image. The creation of a pattern noise image is enabled by recognizing and using the fact that pseudo-projection images are comprised of two image parts. A first image part is stable and common to the entire set of pseudo projections and a second image part which is dynamic and changeable from one projection to the next. The dynamic part is the part that is associated with a sample such as a cell and other material that is suspended in the gel. In an optical tomography system design, the cell changes its position as the capillary tube is rotated. Because the cell and other material are dark relative to the background the gel-suspended part of the image may be thresholded out, leaving a partial representation of the stable part of the image.

Figure 2A:
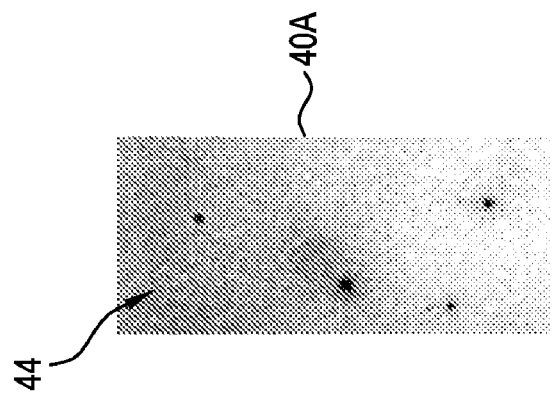
FIG. 2A shows a selected portion of the pseudo-projection image of FIG. 2 that has been enhanced to better visually illustrate some subtle effects of pattern noise.
Figure 2:
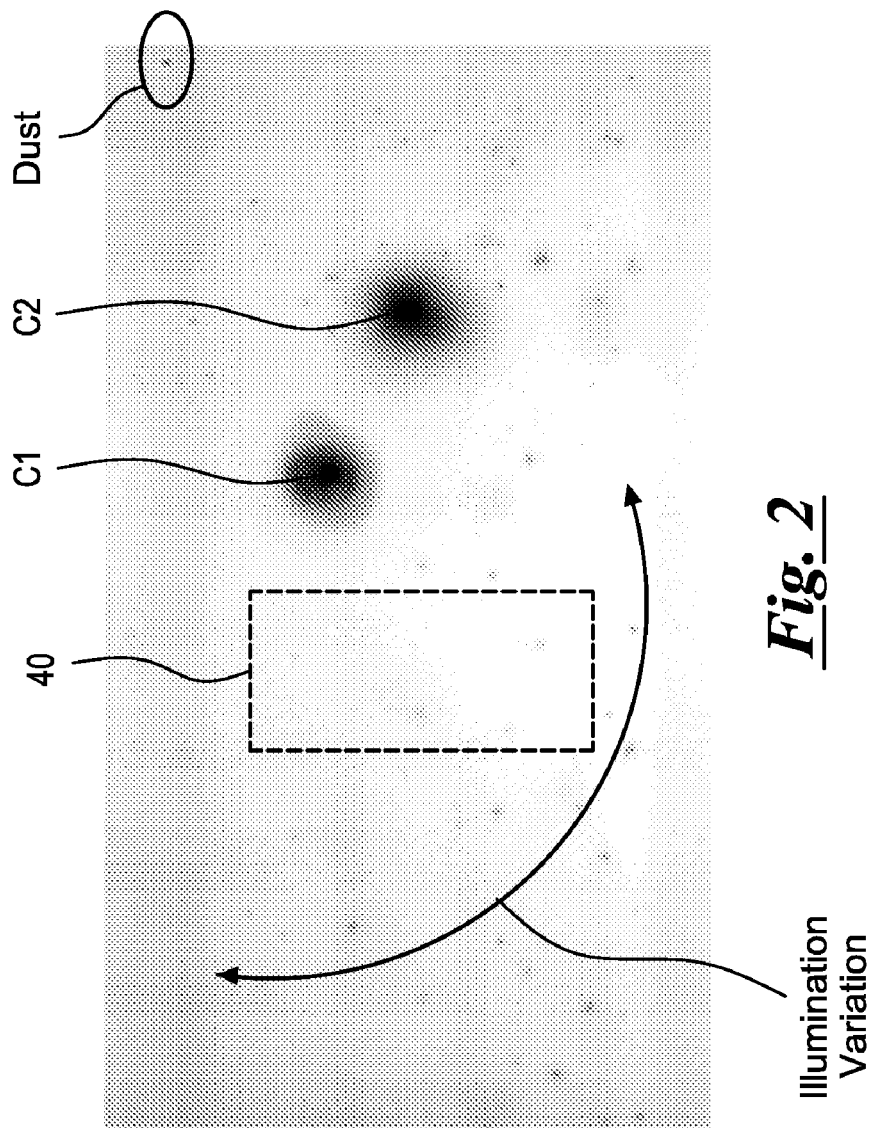
FIG. 2 shows a typical pseudo-projection image with pattern noise.
Figure 4B:
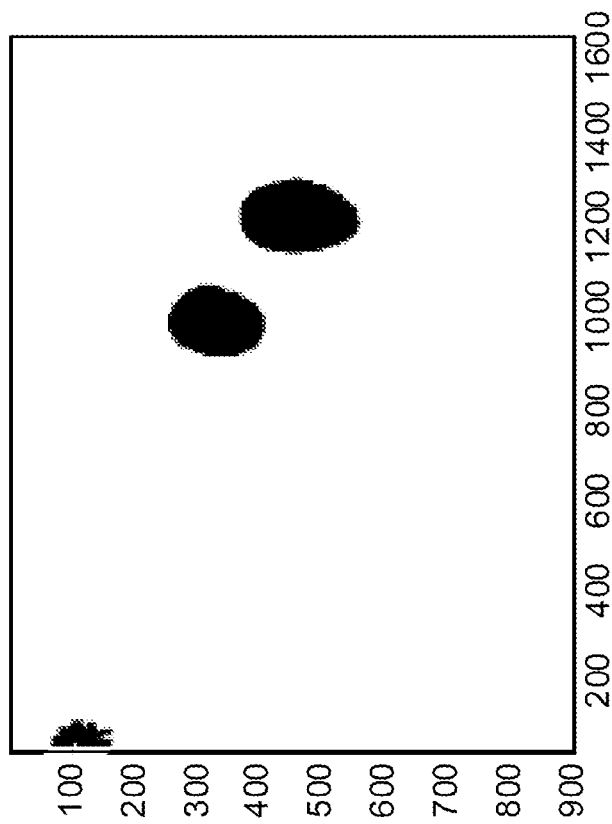
FIG. 4B shows a mask image for the cells.
Figure 4A:
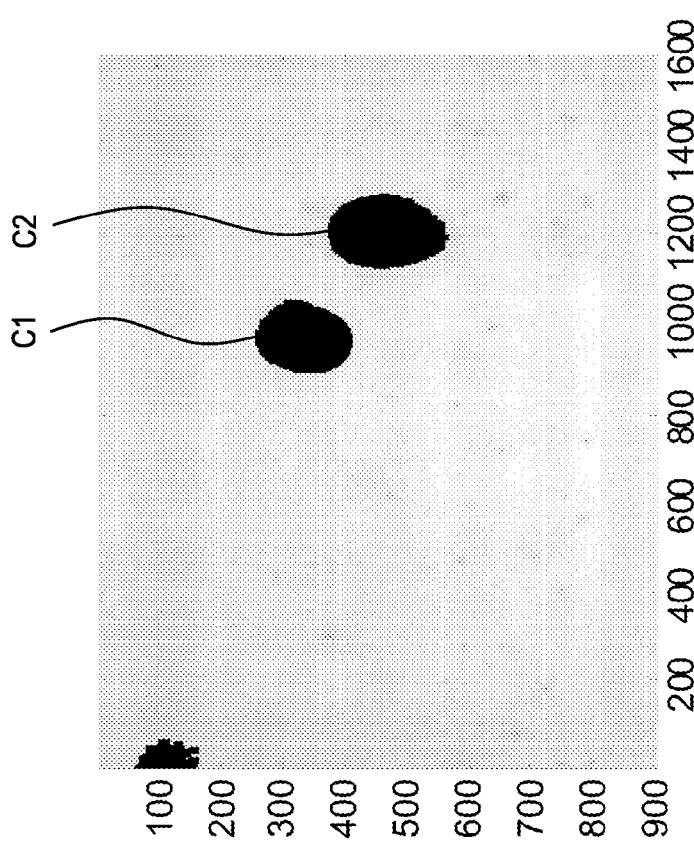
FIG. 4A shows a masked pseudo projection of the cells shown in FIG. 2

An image after application of a threshold is shown for the pseudo projection of FIG. 2 in FIG. 4A. Note that FIG. 4B contains a mask image that is a binary version of the grayscale version of FIG. 4A where all non-zero pixels are set to one. FIG. 5A and FIG. 5B and FIG. 6A and FIG. 6B show similar images for rotations plus and minus 45 degrees respectively from the position represented in FIG. 4A and FIG. 4B. The axes are in pixel counts.

Figure 5B:
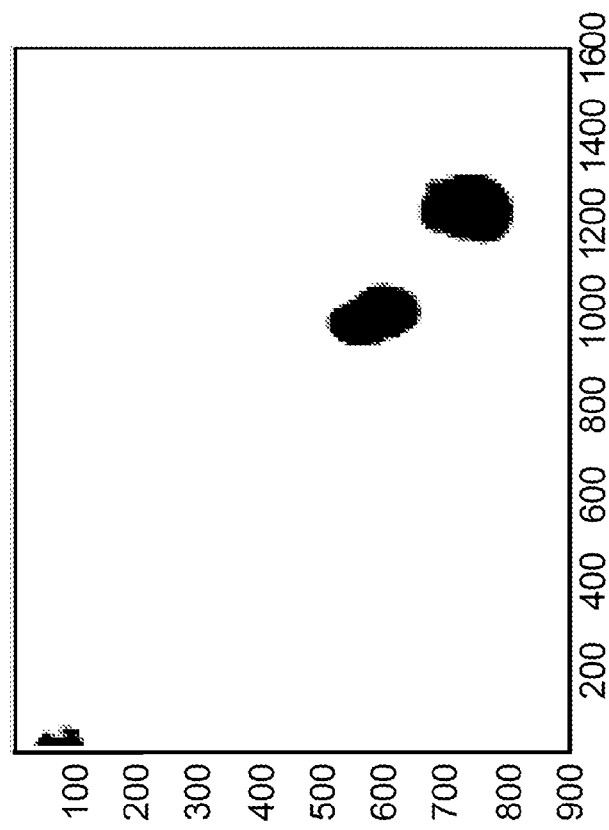
FIG. 5A shows a masked pseudo projection of the cells shown in FIG. 2 with capillary advanced by 45° and FIG. 5B shows a mask image for the cells.
Figure 5A:
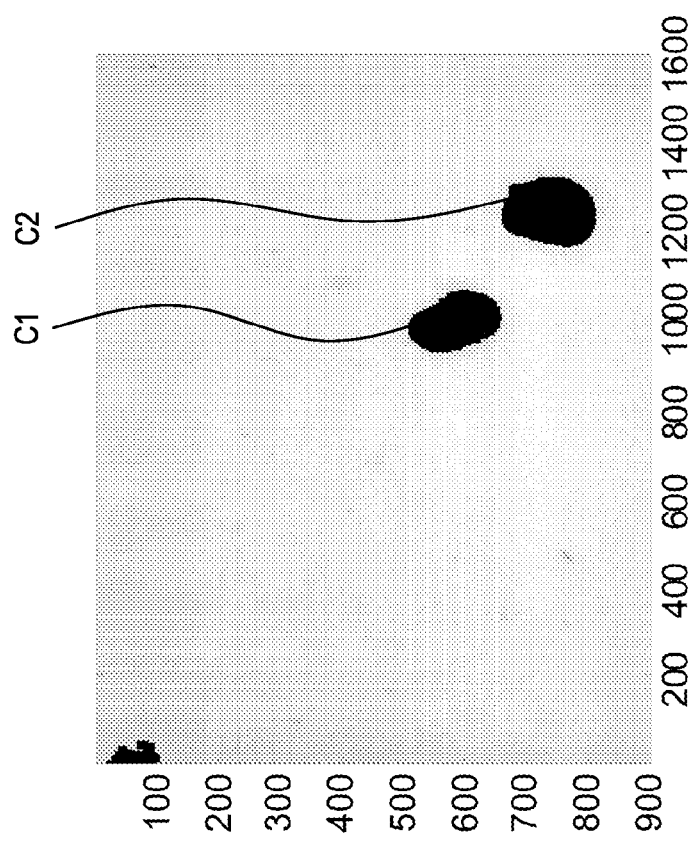
Figure 6B:
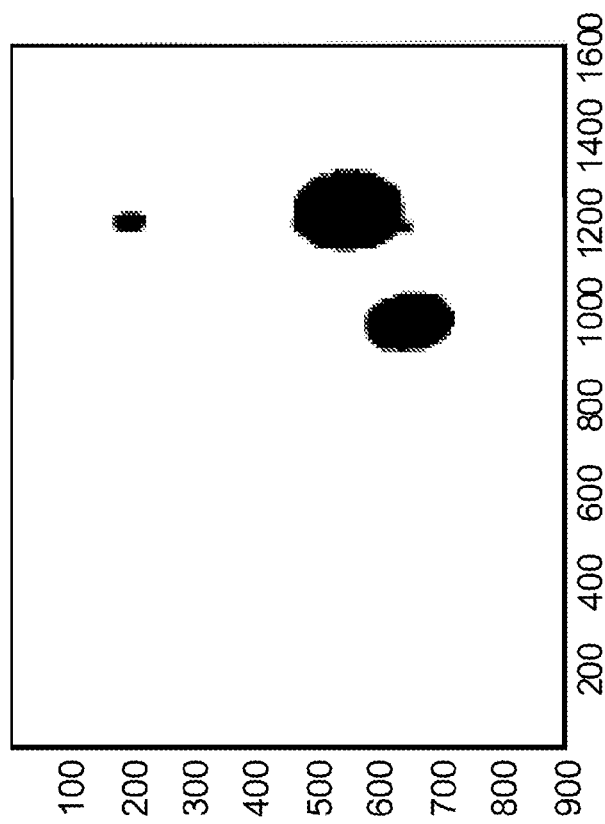
FIG. 6 shows a masked pseudo projection of the cells shown in FIG. 2 with capillary reversed by 45° and FIG. 6B shows a mask image for the cells.
Figure 6A:
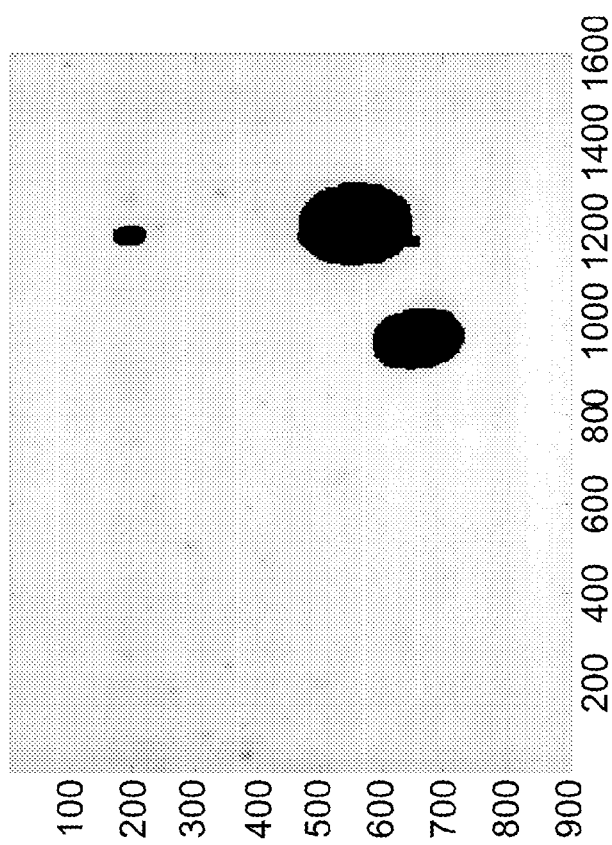
Figure 7:
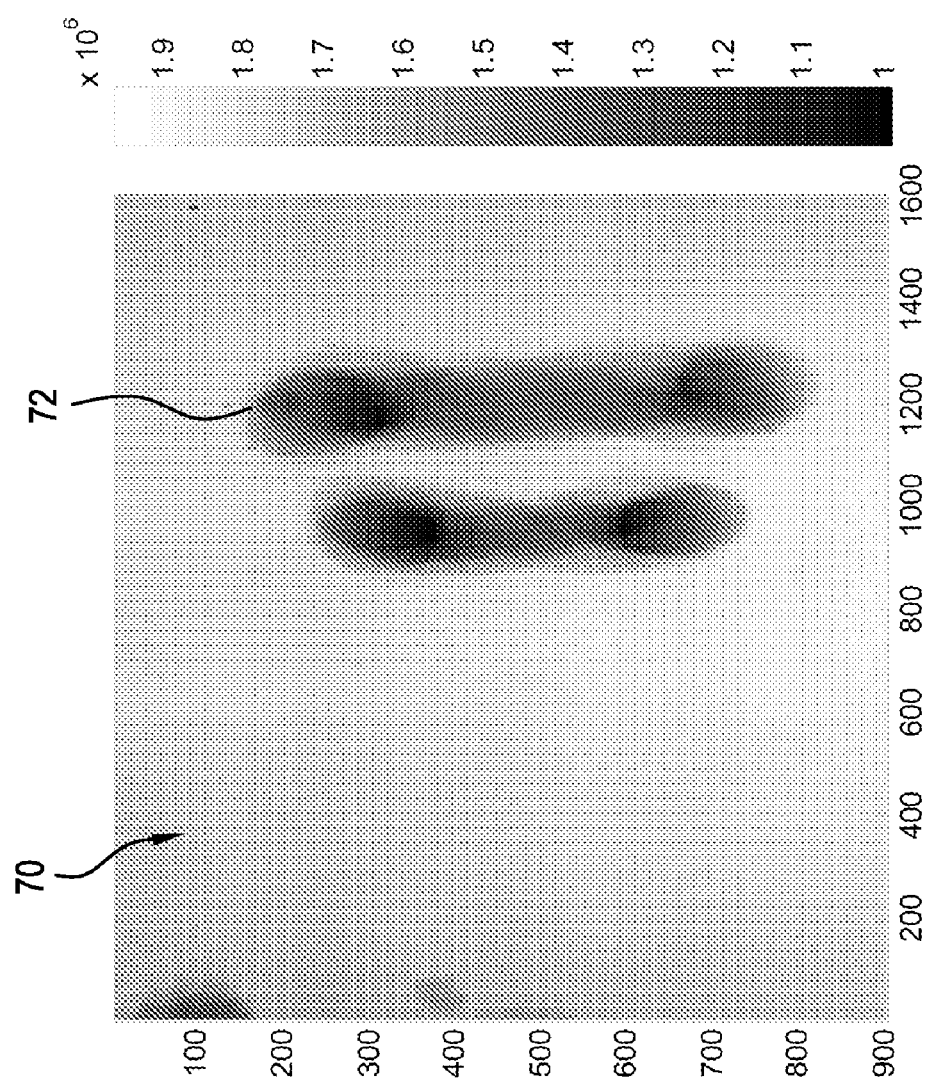
FIG. 7 shows an image resulting from summation of all masked pseudo projections.

Referring now jointly to FIG. 4A, FIG. 5A and FIG. 6A, note that each image contains a different part of the background, or pattern noise containing part of the image. In this observation the key to the formation of the background image is found. The thresholded images for the entire set of masked pseudo-projections may be summed together to form an ensemble grey scale image as shown in FIG. 7 for an entire set of 500 pseudo-projections. It will be understood that, while in some examples a set of 500 pseudo-projections was used, the invention is not so limited and more or less pseudo-projections may be included in a set. The amount and rate of rotation may also be varied for different applications or results.

Referring now jointly to FIG. 4B, FIG. 5B and FIG. 6B the mask images there shown may be summed together to form an ensemble mask. Summed images for an entire set of 500 pseudo-projections are shown in FIG. 8.

Figure 8:
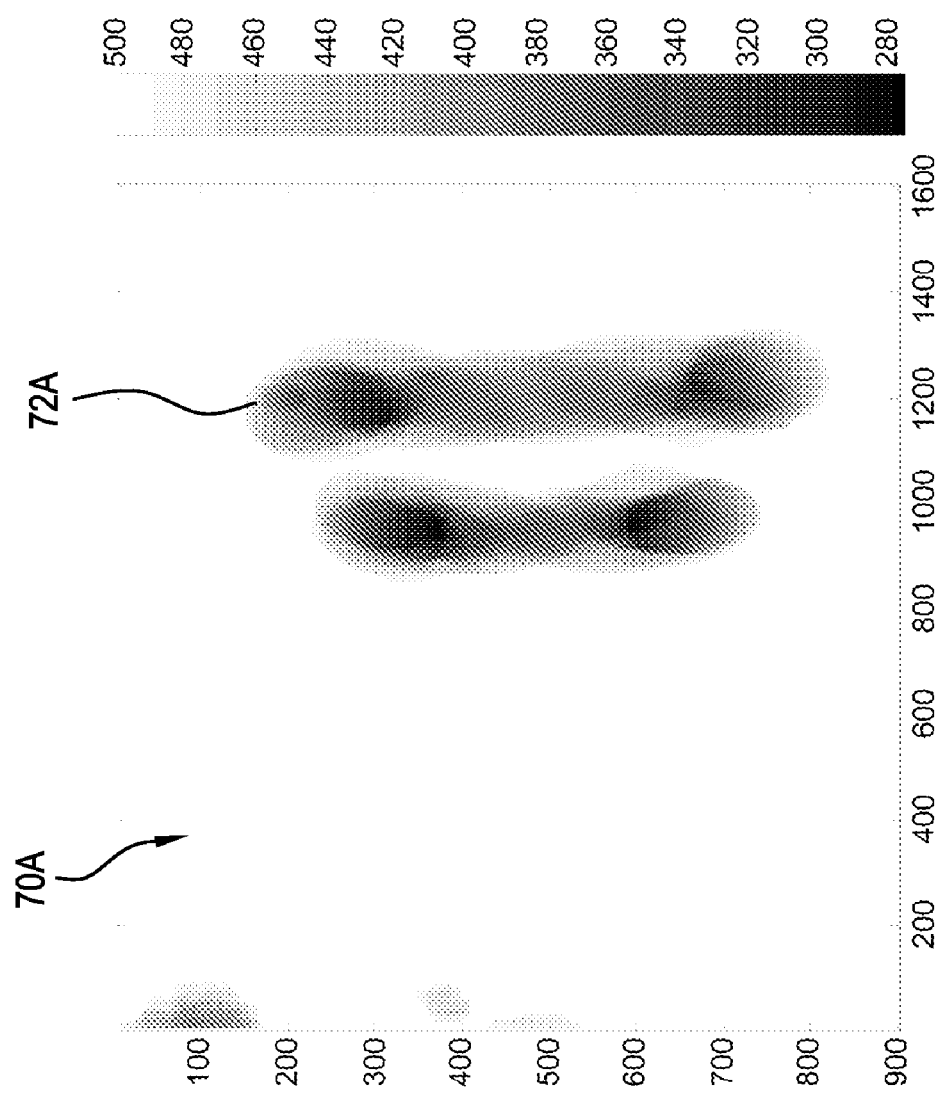
FIG. 8 shows an image resulting from summation of all mask images.

Referring now jointly and respectively to FIG. 7 and FIG. 8 it can be seen that at no spot in the images is there a point where some information concerning the background is not available. By design, the background generally indicated as 70 and 70A in the respective figures is not substantially modulated through rotation of the tube. Cellular material is evidenced by modulated patterns, for example, 72 and 72A in the respective figures. Therefore, it is a good assumption that the background as computed through by averaging all 500 pseudo-projections may be approximated by the background in any one pseudo-projection. As a result, the pattern noise image may be found by dividing the ensemble grey scale image by the ensemble mask.

Figure 9:
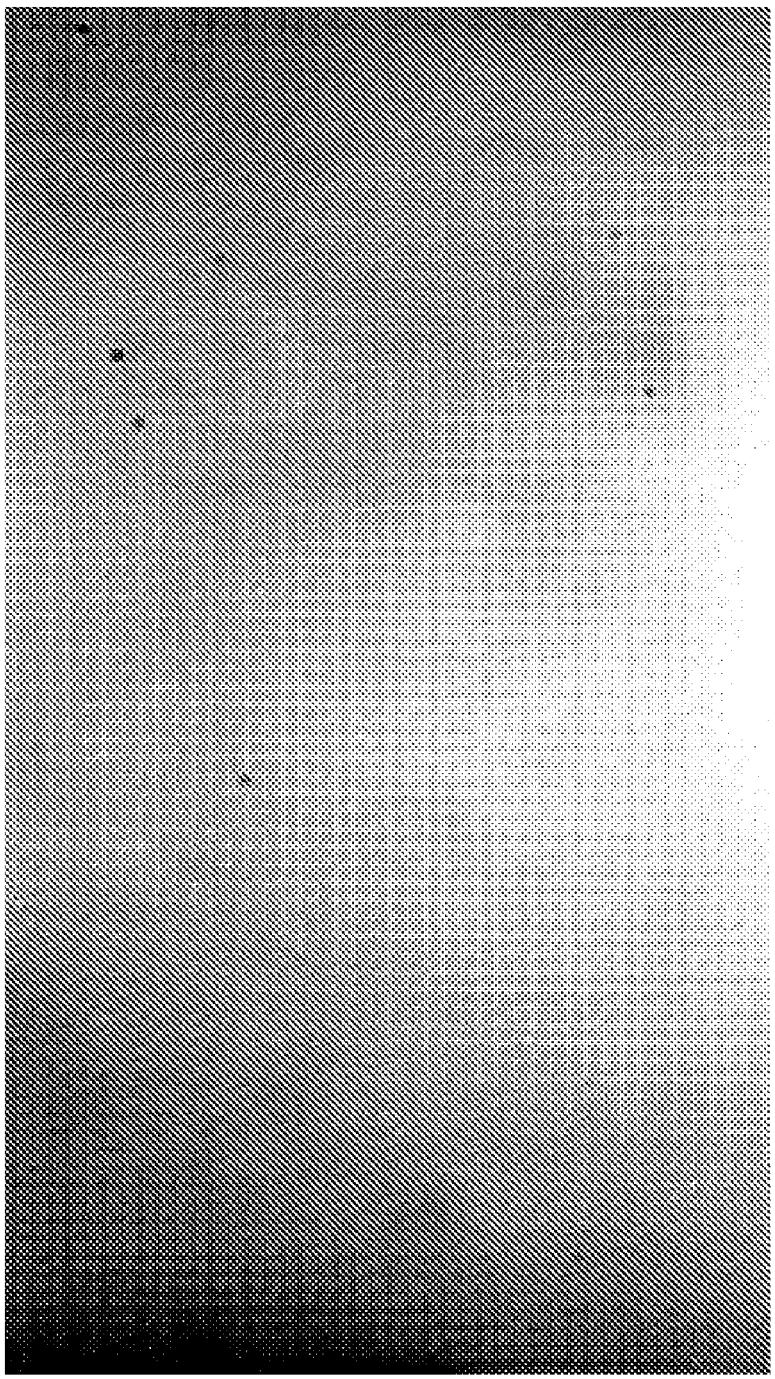
FIG. 9 shows a noise image with grayscale expanded to fill image dynamic range.

The result is shown in FIG. 9 where the noise image has been processed to expand the grey scale range to fill the entire dynamic range for the image. Note that FIG. 9 shows that the noise image represents all the relevant distortions for which a correction is desired including
  a. Illumination variation,
  b. Dust, and
  c. Mottling.
Correction of Any One Pseudo-projection is Then a Matter of Division.

Figure 10:
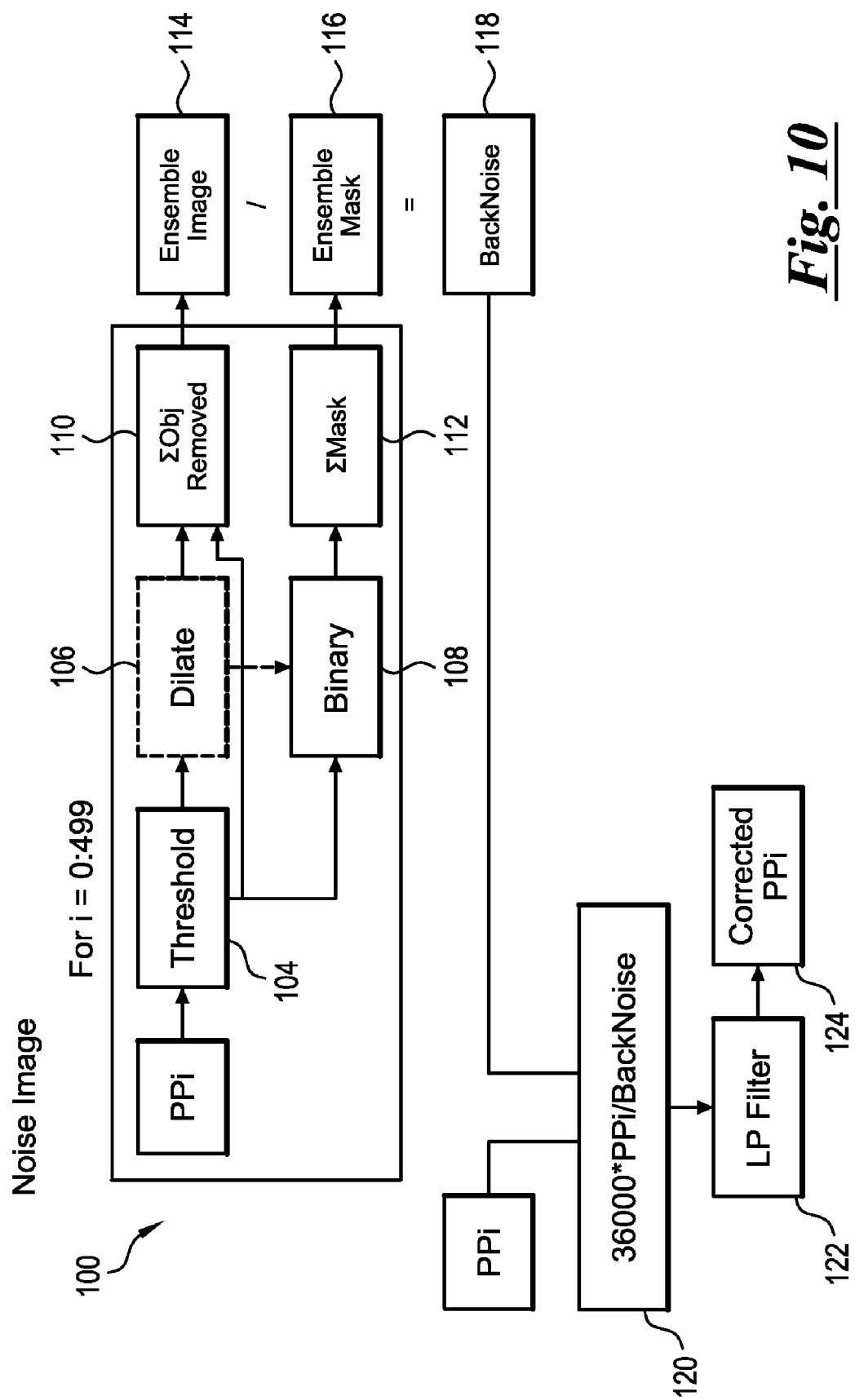
FIG. 10 shows a noise correction schematic.

Referring now to FIG. 10 a noise correction schematic is shown. A typical 3D reconstruction for a biological cell requires acquisition of 500 pseudo-projection images, $PP_0$-$PP_{499}$, each acquired as the capillary tube rotates through 500 incremental rotation angles, where $PP_0$ is acquired at angle 0° and $PP_{499}$ is acquired at about 360°. In operation loop 100 is repeated through 500 incremental angles according to the command i=0:499. Each pseudo projection, $PP_i$, is processed through a threshold operation 104 to produce a threshold image. Optionally, the threshold image may then be dilated 106 to produce a dilated image. However, dilation is not an essential step for pattern noise correction and may be bypassed or left out. The dilated image or threshold image, as the case may be, is sent to a summer 110 which accumulates images with removed objects, and the summation of all images forms an ensemble image 114. The dilated image or threshold image, as the case may be, is also processed into a binary image at 108 to form a mask that is summed at mask summer 112 ultimately producing an ensemble mask 116. Threshold procedures are described further below with reference to FIG. 13. The operations of thresholding, dilating and mask creation may be implemented in a computer as a software program, dedicated processor, computer processor, electronic circuits or the like including processors and related devices listed above.

Figure 13:
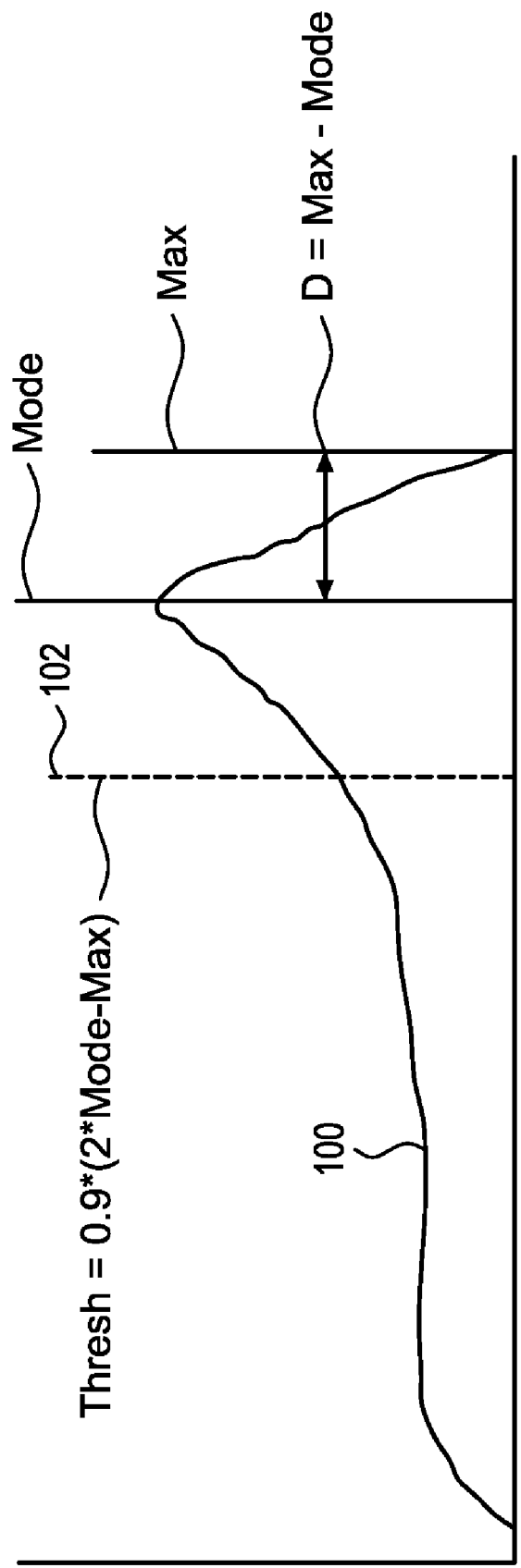
FIG. 13 shows a graphical representation of threshold selection criteria.

Referring now to FIG. 13, a graphical representation of a histogram marked with threshold selection criteria is shown. Correct functioning of the noise correction algorithm depends upon correct selection of the threshold used to remove objects from pseudo-projections. In one example, threshold selection is accomplished through a two-part process and performed separately for each pseudo-projection. The two-part process of threshold selection is based on two principles. First a histogram 100 is generated that combines two influences from the image, the background and that of an object, such as a cell. The histogram 100 is characterized by a mode ("Mode") and a maximum ("Max"). The mode represents the most frequently occurring value, which here is the average value of the background. A cell in the image influences the histogram to its dark side. Hence the variance in the background may be estimated by finding the difference between the maximum and the mode. An initial estimate for the threshold for separating cell from background in the image may therefore be made according to the formula: Thresh=0.9(2*Mode−Max) as indicated by broken line 102. The estimated threshold is then applied to the image and the total area below the threshold is found.

The second principle governing threshold calculation is derived from the fact that a profile of any of the various objects changes little from pseudo-projection to projection. This is because the capillary tube rotates in small increments from one pseudo-projection to the next. This fact is used to further refine the threshold as it is iteratively adjusted until the total area of pixels beneath the threshold is within 10% of the area for the previous threshold.

Referring again to FIG. 10, once the summations are available the ensemble image 114 is divided by the ensemble mask to yield the background pattern noise 118. Each $PP_i$ is multiplied by a scaling factor (here, for example, 360000) and the product is divided by the background pattern noise 118. The quotient image is filtered by a low pass filter 122 that passes low-frequency signals but attenuates signals with frequencies higher than the cutoff frequency, where the cutoff frequency is selected to filter out high frequency artifacts as may be caused, for example, by camera noise. The cutoff frequency is selected so as to preserve the highest spatial frequencies for which response in the reconstruction is desired. A filtered image is produced at 124 as a noise corrected pseudo projection.

Figure 11:
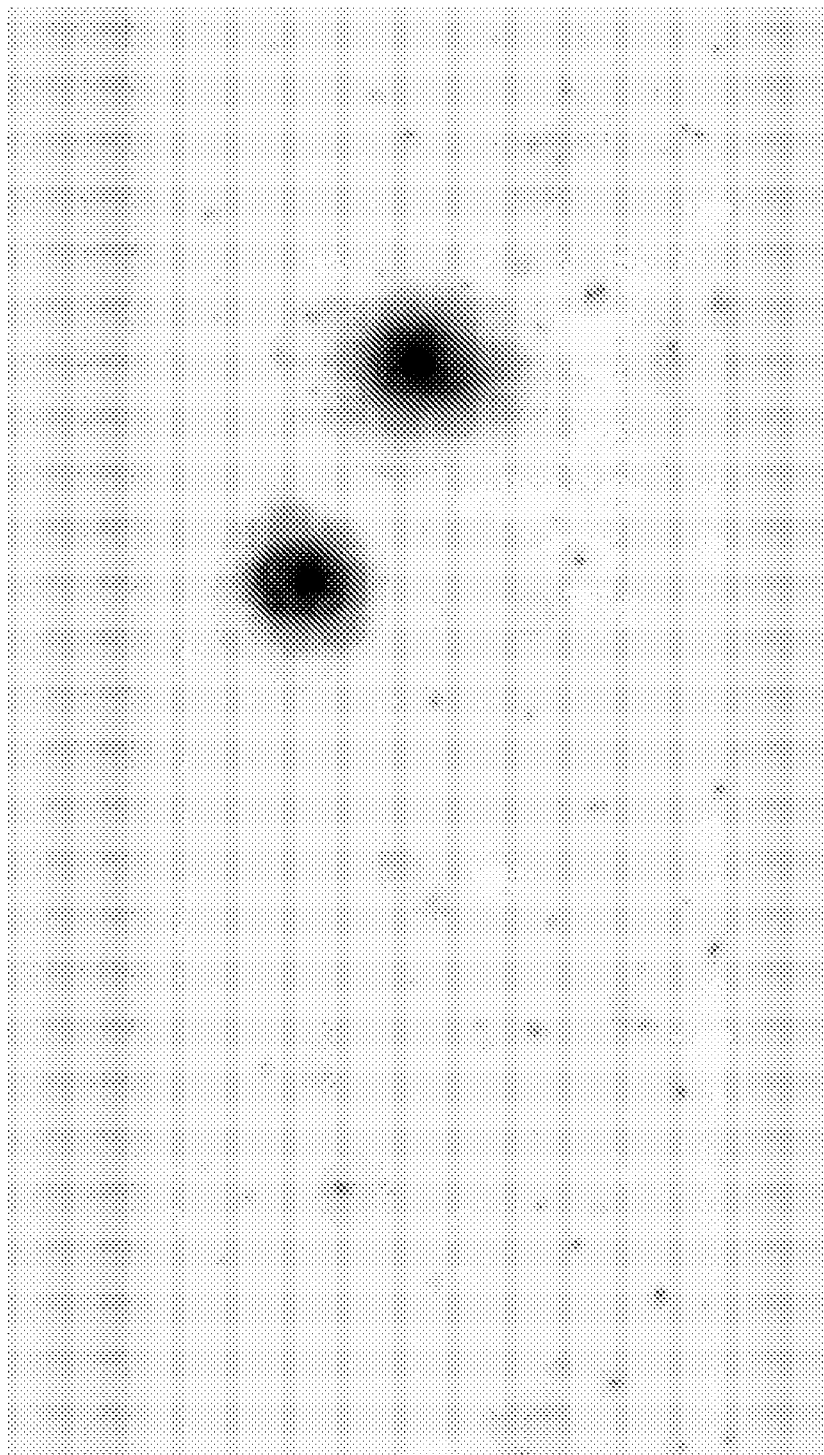
FIG. 11 illustrates the image of FIG. 2 after application of noise correction.

Referring now to FIG. 11, the result of correction for the pseudo-projection of FIG. 2 is shown. A comparison of FIG. 11 with FIG. 2 shows that illumination variation has been corrected, dust removed and mottling substantially reduced.

Figure 12B:
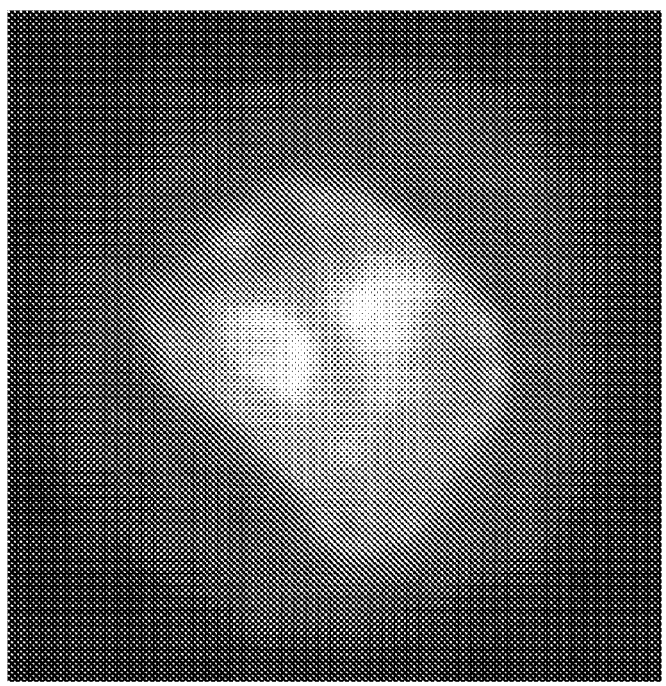
FIG. 12A and FIG. 12B show a comparison of image slices from a 3D reconstruction of pseudo projections without noise correction and with noise correction respectively.
Figure 12A:
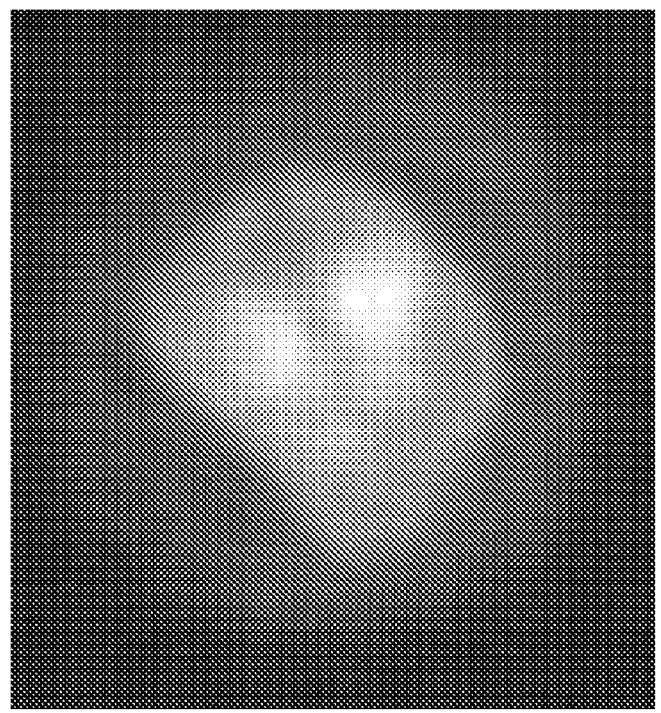

Referring now to FIG. 12A and FIG. 12B, a comparison of image slices from a 3D reconstruction volume of pseudo projections without noise correction and with noise correction respectively is shown. The first image in FIG. 12A resulted from reconstruction with no noise correction. The second image in FIG. 12B has been processed with noise correction. Note the much cleaner presentation of cellular detail for the noise corrected reconstruction.

In an optical tomography system or similar system, noise correction according to the methods and systems described herein may be effectively performed when there is sufficient movement of the cell so that the background may be imaged in at least a small number of pseudo-projections. When this is not the case the noise correction may not be effective. Further, correct execution of the technique depends on the ability to remove the cells from the background so that the grey matter in an image resulting from summation of all masked pseudo projections, as shown, for example, in FIG. 7, represents only the background. This occurs when the algorithm that determines the threshold correctly identifies the threshold to segment cells. When thresholds are incorrectly identified, an image resulting from summation of all masked pseudo projections can include cellular residues which leads to an incorrect normalization. In such a circumstance the resulting pattern noise image, unlike that shown in FIG. 9, exhibits high variance. When variance of the noise image exceeds a predetermined level, noise correction cannot be effectively performed.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A system for correcting pattern noise projection images comprising:
   means for acquiring a set of projection images, where each of the set of projection images is acquired at a different angle of view;
   means for thresholding each projection to produce a set of threshold images, where the thresholding means is coupled to receive the set of projection images;
   means for summing the set of threshold images to form an ensemble image, where the summing means is coupled to receive the set of threshold images;
   means for processing each of the set of threshold images to produce a set of binary images, where the binary processing means is coupled to receive the set of threshold images;
   means for summing the set of binary images to form an ensemble mask, where the summing means is coupled to receive the ensemble mask;
   means for dividing the ensemble image by the ensemble mask to yield a background pattern noise image, where the dividing means is coupled to receive the ensemble image and the ensemble mask;
   means for multiplying each projection image by a scaling factor and dividing by the background pattern noise to produce a quotient image, where the multiplying means is coupled to receive each projection image and the background pattern noise; and
   means, coupled to receive the quotient image, for filtering the quotient image to produce a noise corrected projection image.

2. The system of claim 1 wherein the means for thresholding comprises:
   means for generating a histogram, where the histogram combines a background and object data, and where the histogram is characterized by a mode (Mode) and a maximum (Max); and
   means for estimating a variance in the background by determining the difference between the maximum and the mode.

3. The system of claim 2 wherein the means for thresholding further comprises:
   a first estimating means for separating the object data from background according to the formula: Thresh=0.9 (2*Mode−Max), where Thresh is an initial estimated threshold applied to the image.

4. The system of claim 3 wherein the means for thresholding further comprises:
   means for determining the total area below an estimated threshold; and
   means for iteratively adjusting the estimated threshold until the total area beneath the estimated threshold is within 10% of the area for each previous estimated threshold.

5. The system of claim 1 wherein the means for thresholding comprises means for applying a threshold based on pixel intensity.

6. The system of claim 1 wherein the set of projection images comprise projection images formed by light passing through an object of interest.

7. The system of claim 1 further comprising means for dilating each threshold image to produce a set of dilated images, where the dilating means is coupled to receive the set of threshold images and the dilated images are passed to the means for processing to produce the set of binary images.

8. The system of claim 1 wherein the set of projection images comprise pseudo projections.

9. The system of claim 1 wherein the means for acquiring the set of projection images comprises an optical projection tomography system.

10. The system of claim 9 wherein the set of projection images comprise pseudo-projection images.

11. The system of claim 6 wherein the object of interest comprises a biological cell.

12. The system of claim 6 wherein the object of interest comprises a biological cell having a nucleus.

13. A method for correcting pattern noise projection images, the method comprising the steps for:
    acquiring a set of projection images with an optical tomography system including a processor, where each of the set of projection images is acquired at a different angle of view;
    thresholding each of the set of projection images by operating the processor to produce a set of threshold images;
    summing the set of threshold images by operating the processor to form an ensemble image;
    processing each of the set of threshold images by operating the processor to produce a set of binary images;
    summing the set of binary images by operating the processor to form an ensemble mask;
    dividing the ensemble image by the ensemble mask by operating the processor to yield a background pattern noise image;
    multiplying each projection image by a scaling factor and dividing by the background pattern noise by operating the processor to produce a quotient image; and
    filtering the quotient image by operating the processor to produce a noise corrected projection image.

14. The method of claim 13 further comprising the step of dilating each threshold image by operating the processor to produce a set of dilated images for passing to the processing step to produce the set of binary images.

15. The method of claim 13 wherein the set of projection images comprise pseudo-projection images.

16. The method of claim 13 wherein acquiring the set of projection images comprises operating an optical projection tomography system to acquire pseudo-projection images.

17. The method of claim 13 wherein the set of projection images comprise projection images formed by light passing through an object of interest.

18. The method of claim 17 wherein the object of interest comprises a biological cell.

19. The method of claim 17 wherein the object of interest comprises a biological cell having a nucleus.

20. The method of claim 17 wherein the step for thresholding further comprises:
    generating a histogram, where the histogram combines a background and object data, and where the histogram is characterized by a mode (Mode) and a maximum (Max); and
    estimating a variance in the background by determining the difference between the maximum and the mode.

21. The method of claim 20 wherein the step for thresholding further comprises separating the object data from background according to the formula $$Thresh = 0.9*(2*Mode - Max),$$

where Thresh is an initial estimated threshold that is applied to the image.

22. The method of claim 21 wherein the step for thresholding further comprises:
    determining the total area below an estimated threshold; and
    iteratively adjusting the estimated threshold until the total area of pixels beneath the threshold is within 10% of the area for each previous threshold.

* * * * *